United States Patent
Louis

(10) Patent No.: US 9,892,321 B2
(45) Date of Patent: Feb. 13, 2018

(54) USING MAXIMAL INSCRIBED SPHERES FOR IMAGE-BASED ROCK PROPERTY ESTIMATION

(71) Applicant: New England Research, Inc., White River Junction, VT (US)

(72) Inventor: Laurent Louis, White River Junction, VT (US)

(73) Assignee: New England Research, Inc., White River Jct., VT (US)

(*) Notice: Subject to any disclaimer, the term of this patent is extended or adjusted under 35 U.S.C. 154(b) by 0 days.

(21) Appl. No.: 15/181,820

(22) Filed: Jun. 14, 2016

(65) Prior Publication Data
US 2016/0379356 A1    Dec. 29, 2016

Related U.S. Application Data

(60) Provisional application No. 62/185,567, filed on Jun. 27, 2015.

(51) Int. Cl.
| | |
|---|---|
| G06K 9/00 | (2006.01) |
| G01B 11/06 | (2006.01) |
| G01N 33/24 | (2006.01) |
| G01N 15/08 | (2006.01) |
| E21B 49/00 | (2006.01) |

(52) U.S. Cl.
CPC ........... G06K 9/0063 (2013.01); E21B 49/00 (2013.01); G01B 11/06 (2013.01); G01N 15/088 (2013.01); G01N 33/24 (2013.01)

(58) Field of Classification Search
CPC .... G01N 33/24; G01N 23/046; G01N 15/088; G06T 2207/10081; G06T 7/11
USPC ............................ 382/109; 702/156; 703/10
See application file for complete search history.

(56) References Cited

U.S. PATENT DOCUMENTS

| | | | | |
|---|---|---|---|---|
| 9,348,056 B2* | 5/2016 | Fredrich | ............. | G06F 17/5018 |
| 2013/0262028 A1* | 10/2013 | De Prisco | ............. | G01N 33/24 |
| | | | | 702/156 |

FOREIGN PATENT DOCUMENTS

WO    2012188868 A2    9/2012

* cited by examiner

Primary Examiner — Charlotte M Baker
(74) Attorney, Agent, or Firm — Richard A. Fagin

(57) ABSTRACT

A method for analyzing a rock sample comprises analyzing a three dimensional image of the rock sample using maximal inscribed sphere analysis to determine proxies for at least one of grain size distribution, mean grain size and standard deviation of grain size. The proxy or proxies are used to determine at least one mechanical property of the rock formation.

16 Claims, 3 Drawing Sheets

USING MAXIMAL INSCRIBED SPHERES FOR IMAGE-BASED ROCK PROPERTY ESTIMATION

CROSS REFERENCE TO RELATED APPLICATIONS

Priority is claimed from U.S. Provisional Application No. 62/185,567 filed on Jun. 27, 2015.

STATEMENT REGARDING FEDERALLY SPONSORED RESEARCH OR DEVELOPMENT

Not Applicable

NAMES OF THE PARTIES TO A JOINT RESEARCH AGREEMENT

Not Applicable.

BACKGROUND

This disclosure relates to the field of estimating physical properties of rock formations using images of samples of the formations. More specifically, the disclosure relates to the use of images of the rock mineral grain portion of the sample, rather than the void space, to estimate one or more physical properties of the rock formation.

Mechanical response to depletion, which comprises irrecoverable volumetric strain as well as elastic deformation, strongly depends on in situ conditions and on the nature of the corresponding perturbation in terms of stress path, strain rate, fluid substitution, etc. The ability to forecast this behavior, whether for pressure support or subsidence risk assessment, hinges on our understanding of deformation mechanisms at the scale of the aggregate, their interplay with preexisting heterogeneities and their manifestation at the scale of the reservoir.

Modeling of mechanical properties traditionally relies on microstructural parameters such as porosity, mineralogy, coordination number, cemented contact area, grain size and shape, which are combined to account for trends obtained in laboratory measurements. The now widespread availability of 3D pore scale imaging techniques allows one to access the intimate make-up of a rock, offering in principle a means to fully quantify and validate the parameters used for pore-scale modeling. It also provides an opportunity to identify which of these parameters control resulting behavior, whether redundancies exist from a physical point of view, and whether they can even be measured in a meaningful way. The option of performing direct numerical simulations based on pore scale images is being increasingly utilized to complement costly laboratory measurements. See, for example, Fredrich, J. T., D. L. Lakshtanov, N. M. Lane, E. B. Liu, C. S. Natarajan, D. M. Ni, and J. J. Toms, 2014, *Digital Rocks: Developing an emerging technology through to a proven capability deployed in the business*. Proceedings of the Society of Petroleum Engineers Annual Technical Conference and Exhibition, Amsterdam, The Netherlands, 27-29 October.

However, an understanding of the key controls of the observed behavior remains essential for generalizations to be made.

Several approaches to compaction modeling exist depending on the application. In basin modeling and pore pressure prediction, empirical relations of exponential and power law types are often used as porosity predictors. In soil mechanics, the Cam-clay model relates the logarithm of applied pressure to the void ratio to describe both elastic and permanent deformation. For cohesive siliciclastic aggregates, yet other approaches have been proposed that use fracture mechanics to establish the conditions for grain crushing and/or pore collapse to occur. In the case of a porous sandstone as observed from a laboratory test perspective, an objective of an image-based technique would be the ability to predict an arbitrary stress path. Such prediction may use the pre-yield elastic behavior, the conditions for the onset of grain crushing and maximum rate of inelastic compaction. Such results could then be input into well-known geomechanical models for reservoir behavior forecasting as a result of depletion.

There continues to be a need for improved methods for interpreting images of rock formation samples to infer mechanical properties of the formations.

DETAILED DESCRIPTION

Figure 1A:
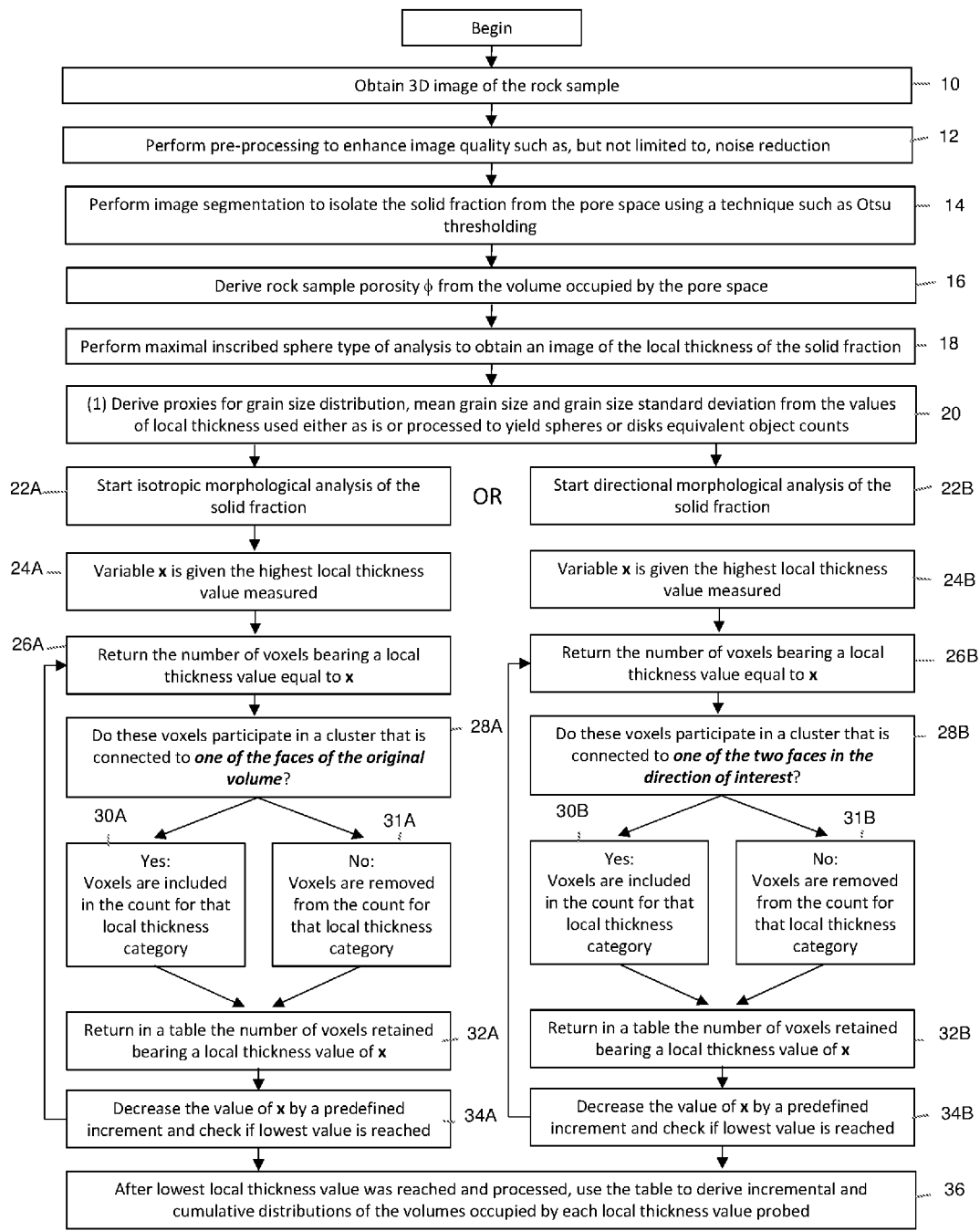
FIG. 1A shows a portion of a flow chart of a method according to one embodiments.

The experimental basis for the present disclosure is related to the stress conditions for failure under hydrostatic loading. Results from experiments on two porous sandstones, the Castlegate sandstone (porosity ~26%) and the Boise sandstone (porosity ~29%), reveal a very large difference (ratio of 3.7) between the pressures needed to initiate grain crushing and accelerated compaction, designated as P*.

As a means of accessing microstructural parameters that are thought to control mechanical behavior, the mineral framework of the samples was tested using a morphological analysis tool that has already been successfully applied to the simulation of mercury injection capillary pressure experiments in pore networks. Starting from micron-scale resolution X-ray CT images of both studied sandstone formations, the workflow consists of first performing a maximum inscribed sphere (MIS) analysis on the mineral framework to obtain some information about grain size and grain size distribution, then using the MIS result to simulate an injection that has the potential to provide a measure of a controlling intergranular contact radius.

In the following disclosure, after describing the mechanical data acquired during hydrostatic loading experiments, a description of the morphological analysis according to the present disclosure is provided to yield proxies for average grain size and characteristic intergranular contact radius. The information of a characteristic intergranular contact radius provides an additional parameter that has the potential to refine the expression of P* as a function of microstructural parameters as proposed in the model by Zhang and Wong [4-5]. The advantage of adding this new independent parameter (the characteristic intergranular contact radius) is to render the ratio of intergranular contact radius to grain radius pressure and strain dependent, thus allowing for better description of failure envelopes as well as post-yield hardening behavior. Also, the proposed image analysis may offer an attractive alternative to digital grain separation, which is a computationally costly and difficult in natural aggregates.

The porosity and mineral composition for the Castlegate and Boise sandstones are provided in TABLE 1. The porosity difference between the two formations is moderate, although the Boise sandstone exhibits a comparatively high plug scale heterogeneity (both in porosity and grain size). Concerning the mineral composition, the main difference between the two rocks is the presence of a substantial amount of feldspar in the Boise sandstone and some amount of carbonate in the Castlegate sandstone.

TABLE 1

| Formation | Castlegate | Boise |
| --- | --- | --- |
| Porosity (%) | 26 | 29 |
| Mineralogy (%) | Quartz (85), Calcite/dolomite (10), Clay (5) | Quartz (45), Feldspar (45), Biotite (5), Clay (5) |

Hydrostatic loading experiments were conducted at New England Research, Inc., White River Jct., VT on plugs of formation samples approximately 1 inch (25 mm) in diameter and two inches (51 mm) in length. The samples were saturated with tap water and the pore pressure was kept constant at 5 MPa (725 PSI) throughout the experiments. Hydrostatic pressure was then applied, increasing at a rate of 2.5 MPa (360 PSI) per minute up to a final pressure of 180 MPa (26100 PSI) for the Boise sandstone and 300 MPa (43500 PSI) for the Castlegate sandstone. Volumetric strain was obtained from the volume of expelled pore fluid.

X-ray CT imaging was performed on samples of the two above described formations by FEI Company, 16700 Park Row Drive, Houston, Tex. 77084 using a HeliScan micro CT scanner on 9 mm diameter plug samples of the two formations in the vicinity of the core samples used for the fluid pressure experiments. The voxel dimensions obtained in the images are 4.29 µm for the Boise sandstone and 3.47 µm for the Castlegate sandstone. From each of these images, a few regions of interest of $300^3$ and $400^3$ voxels$^3$ were selected for image analysis. Segmentation into pore and solid phases was conducted using default Otsu thresholding (segment at grey level that minimizes intra-phase variance) available in ImageJ [7]. The maximum inscribed sphere analysis was performed using the implementation of Dougherty and Kunzelmann [8] available as a plugin in ImageJ under the name "Local Thickness". The principle of this analysis is to find and tag each voxel with the diameter of the largest sphere containing that voxel that can be fit inside the analyzed 3D object. The injection simulation into the mineral framework was implemented using ImageJ Macro language and consists of sequentially capturing clusters connected to the injection faces (6 for isotropic injection and 2 for directional injection) in step by step segmentation starting from the largest local thickness.

During testing it was determined that the Boise sandstone exhibits a much lower critical pressure P* (60 MPa or 8700 PSI) than the Castlegate (220 MPa or 31900 PSI), with a ratio of 3.7 between the two values. The Boise sandstone exhibited a fairly stable compaction regime in the Boise sandstone until enhanced hardening was observed. If continued further, it is expected that these stress vs. strain curves would start exhibiting a progressively more elastic behavior, reducing plastic compaction to a transient phenomenon, as suggested in the probabilistic damage model of Zhu et al. [9] (though this was applied to permeability modeling during shear-enhanced compaction). A fully predictive compaction model should be able to provide as a function of the stress path (i) an elastic loading modulus, (ii) the stress conditions for the onset of grain crushing or substantial irrecoverable deformation and (iii) the rate at which this compaction occurs.

From the CT images, subvolumes representing about 5 mm$^3$ of material were extracted for the maximum inscribed sphere analysis. The pore space in the CT images was segmented and MIS analysis was performed. MIS analysis reveals constriction that occurs at grain boundaries resulting in smaller maximal inscribed sphere or local thickness.

Cumulative distribution of the MIS results for all the subvolumes considered (4 subvolumes for Castlegate and 3 for Boise) together with 2 examples identified according to their local thickness indicate that for the two different formations the MIS distributions are clearly distinct and suggest for the Castlegate formation compared to the Boise formation: (1) a smaller mean grain size; (2) a narrower grain size distribution; and (3) a more homogeneous microstructure. The Boise formation subvolumes were selected from two zones that appeared clearly different on the full size CT image, whereas no notable difference from one zone to another could be observed in the Castlegate formation.

The foregoing experiments show that the MIS results already provide useful proxies for microstructural parameters. Next, the equivalent of a drainage simulation on the mineral framework was performed to test whether there exists a characteristic radius that controls the interconnectivity within the aggregate.

Simulated mercury injection curves exhibit the same characteristics as MICP data in the sense that a conformance effect can be observed in the early stages of the injection (artifact associated with asperities directly in contact with the surface), but more importantly that there exists a radius for which a maximum incremental intrusion is observed, before the mineral framework becomes fully saturated through ever smaller increments. This radius which may be referred to as "characteristic intergranular contact radius" Rcc is a parameter that may be related to amplification of the stress effectively experienced by the grains when loading the aggregate.

To associate with Rcc, one may seek a measure of a grain size that corresponds to the state of the aggregate at the time of 'breakthrough' Rgc. To do that, the MIS data that belongs to the cluster invaded at breakthrough can be used.

The subset of the local thickness distribution can then be used to estimate Rgc. In the present case a simple average of the local thickness values was used. The values obtained in all subvolumes of Castlegate and Boise formations for Rcc and Rgc are provided in Table 2.

TABLE 2

| | Fm. | | | | | | |
| --- | --- | --- | --- | --- | --- | --- | --- |
| | Castlegate | | | | Boise | | |
| Zone | 1 | 2 | 3 | 4 | 1 | 2 | 3 |
| Rcc (+/−4 µm) | 42 | 47 | 47 | 47 | 67 | 53 | 67 |
| Rgc (+/−4 µm) | 55 | 60 | 61 | 61 | 105 | 75 | 102 |

The microstructural parameter proxies that can be derived from this study may include porosity (through initial segmentation), grain size distribution (direct MIS result), characteristic intergranular contact radius Rcc and a characteristic grain radius Rgc which corresponds to the average radius of the connected grains at the time of maximum intrusion.

The data obtained by the MIS analysis is not strictly a grain size distribution in the sense of a count but rather a distribution of volumes occupied by grains of given diameters or radii. One may propose to normalize these statistics by the square of the radius (assuming a pipe geometry) or by the cube of the radius (assuming a spherical geometry) to approach quantities that would be closer to actual counts. There may be some question whether counts should actually be used since volume fractions may be considered more appropriate for an effective medium type of approach. The MIS distribution was used as is in the present disclosure The micromechanical model disclosed by Zhang et al., 1990 [4] which is based on Hertz theory, proposes to predict the pressure P* necessary for the onset of inelastic compaction induced by grain fracturing and pore collapse. The foregoing analysis, which invokes the mode I of opening of a microcrack at the grain-to-grain contact as a means for initiation of grain crushing, was reused more recently to model shear-enhanced compaction by Brzesowsky et al., 2014 [10]. As recast in Wong et al., 1997 [5], and in accordance with the micromechanical model of Zhang et al., (4) the value of P* is showed to be primarily controlled by a power of the product ($\Phi R$) where $\Phi$ is the porosity and R is the mean rock grain radius. More specifically, the model predicts that P* may be proportional to $(\Phi R)^{-3/2}$. Scatter, however, suggests that other parameters are likely to affect the results obtained.

Using the values we obtained in the morphological analysis, the expression of Zhang et al. predicts a P* ratio between the Castlegate and Boise sandstones in the range 1.6 to 3.1 with an average of 2.3, what is somewhat lower to the ratio of 3.7 observed in the hydrostatic experiment. It is clear that many other factors, some of which will be listed below, are likely to contribute to this matching exercise. As a first order improvement it is proposed that the information of the characteristic contact radius be incorporated into an expression for P* in the form an intensification factor $\gamma = (Rcc/Rgc)^2$.

The dependency over $R^{-3/2}$ in the expression of Zhang et al. or even simply over $R^{-1}$ is appealing as it corresponds to the observation that strength tends to decrease with sample size increase, which can be intuitively understood as the effect of an increasing probability of finding defects as the dimensions increase or as the fact that once division of a particle has occurred due to the presence of a weakness, the resulting two particles are in essence devoid of that weakness.

Taking into account that dependency of strength over length scale, and rewriting P* the way the porosity contributes to the strength so that finite boundaries are set, it is proposed to rewrite partially P* in the following fashion:

$$P^* \propto \frac{1-\Phi}{R_{gc}}\gamma \quad (1)$$

If it is accepted that there exists a scale dependency of the strength, a reference may be set that would balance Eq. (1) in terms of physical units and provide a value to use if the porosity tends towards zero. The foregoing may be expressed as:

$$P^* \propto \sigma^*_{ref} R_{ref} \frac{1-\Phi}{R_{gc}}\gamma \quad (2)$$

where a reference mineral strength is added together with the length scale at which that reference is valid. The reference mineral strength also provides a means to introduce an effective mineralogical contribution which is thought to exert substantial influence on inelastic compaction behavior.

Figure 1B:
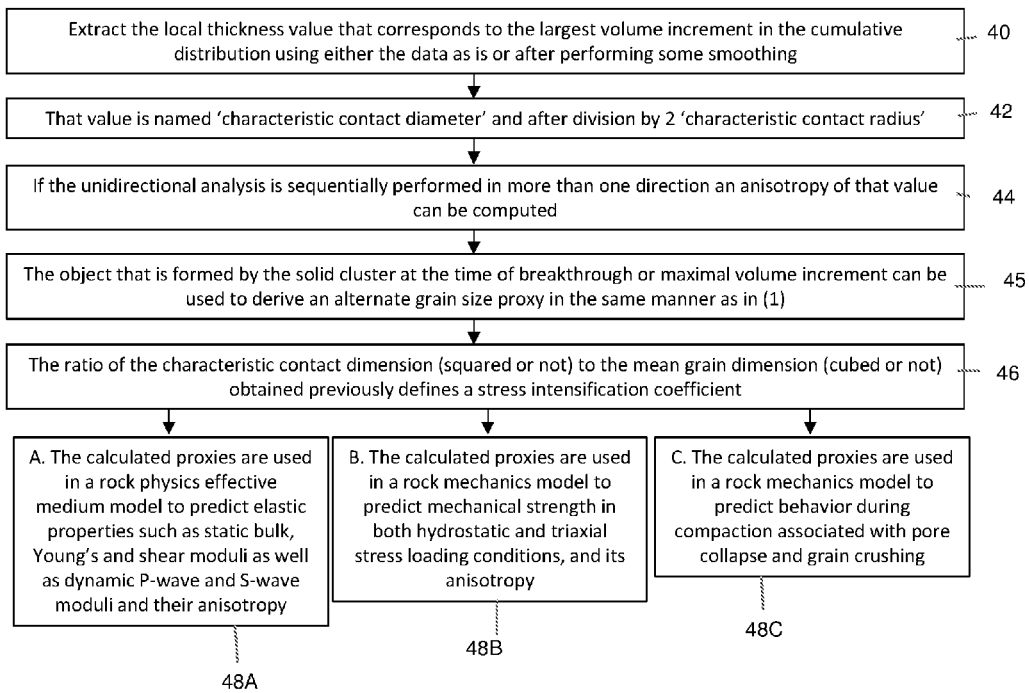
FIG. 1B shows the remainder of the flow chart in FIG. 1A.

Having explained the theoretical foundation and test results for a method according to the present disclosure, an example implementation will now be explained with reference to FIGS. 1A and 1B. Referring first to FIG. 1A, at 10, a 3D image of the rock sample is obtained. At 12, pre-processing to enhance image quality may be performed, for example and without limitation, noise reduction. At 14 image segmentation may be performed to isolate the solid fraction from the pore space using a technique such as Otsu thresholding. At 16, rock sample porosity $\Phi$ may be determined from the volume occupied by the pore space in the image.

At 18, maximal inscribed sphere type of analysis may be performed to obtain an image of the local thickness of the solid fraction of the formation. The objective of such analysis consists of tagging each volume element (voxel) of the domain analyzed with the diameter (hence the concept of local thickness) of the largest sphere inscribed in the domain and containing that voxel. Examples of implementation can be found in references [2] and [8]. At 20, proxies may be derived for grain size distribution, mean grain size and grain size standard deviation from the values of local thickness used either as is (e.g., by considering that the distribution of the local thicknesses directly yields a relevant proxy for grain size distribution as applies to the physical property of interest) or processed to yield, for example, spheres or disks as equivalent object counts. If the solid fraction is idealized as an aggregate of substantially spherical particles, then the particle count can be obtained by dividing the population of each bin in the distribution by the volume of the sphere corresponding to the diameter or thickness associated with that bin (e.g., $4/3\pi(d/2)^3$). If the solid fraction is idealized as a set of two-dimensional disks (tube-like geometry), then the particle count can be obtained by dividing the population of each bin in the distribution by the cross sectional area corresponding to the diameter or thickness associated with that bin (e.g., $\pi(d/2)^2$).

At 22A, isotropic morphological analysis of the solid fraction may be performed. This signifies that the injection simulation will be conducted from all sides of the probed volume simultaneously. At 24A a variable x is given to the highest local thickness value measured. At 26A, the number of voxels bearing a local thickness value equal to x is returned. At 28A, a decision element is made based on whether returned voxels individually participate in a cluster that includes all previously retained voxels (except for the first stage where no voxels have been retained yet) and that is connected to one of the faces of the original volume. If yes, i.e., for those voxels that passed the foregoing test, at 30A, those voxels are included in the count for that local thickness category. If no, i.e., for those voxels that failed the test, at 31A, those voxels are ignored. At 32A, the number of voxels retained bearing a local thickness value of x are returned to a table. At 34A, the value of x is decreased by a predefined decrement ensuring that no voxels will be ignored by the analysis, and a check is performed to determine if a lowest value is reached. If the lowest value is not reached, the process returns to 26A and the analysis in blocks 28A, 30A, 31A, 32A sand 34A is repeated until at 34A the lowest value is reached. At 36, the resulting table bears a distribution of volumes that constitute the sequential increments that are invaded when simulating the acquisition of a 'mercury injection capillary pressure' (MICP) curve. The increments in that distribution can be sequentially added to create a cumulative distribution starting from the volumes corresponding to the largest local thickness.

At 22B through 34B, the same process as in 22A through 34A is started with the difference between processes being that the process beginning at 22B will be conducted by checking for connectivity to either of one pair of volume faces at a time along a direction of interest, hence the denomination of directional morphological analysis. This process ends at 36 as for the isotropic process of 22A through 34A with a similar result table.

At 40, the local thickness value is extracted that corresponds to the largest volume increment in the cumulative distribution using either the data as is or after performing some smoothing. At 42, the extracted local thickness value is named the "characteristic contact diameter" and after division by 2, the "characteristic contact radius." At 44, the directional analysis of 22B may be sequentially performed in more than one direction and an anisotropy of the characteristic contact radius value can be computed.

At 45, the object that is formed by the solid cluster at the time of largest volume increment, which corresponds to the characteristic contact diameter, can be used to derive an alternate proxy for grain size distribution, mean grain size and grain size standard deviation following the same procedure as in step 20 and as At 46, a ratio of the characteristic contact dimension (squared or not) with respect to the mean grain dimension (cubed or not) obtained previously defines a stress intensification coefficient γ.

At 48A, the calculated proxies may be used in a rock physics effective medium model to predict elastic properties such as static bulk modulus, Young's modulus and shear modulus, as well as dynamic P-wave and S-wave moduli and their anisotropy. At 48B, The calculated proxies may be used in a rock mechanics model to predict mechanical strength in both hydrostatic and triaxial stress loading conditions, and the anisotropy thereof. At 48C, the calculated proxies may be used in a rock mechanics model to predict behavior during compaction associated with pore collapse and grain crushing (e.g., as may be caused by fluid pressure depletion in a porous subsurface formation).

Figure 2:
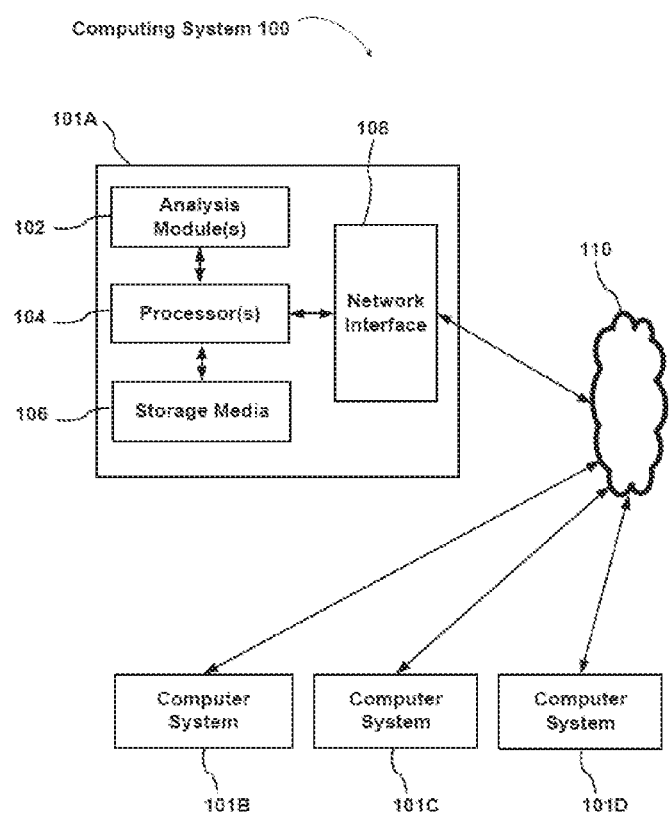
FIG. 2 shows a computer system that may be used in some embodiments.

FIG. 2 shows an example computing system 100 in accordance with some embodiments. The computing system 100 may be an individual computer system 101A or an arrangement of distributed computer systems. The individual computer system 101A may include one or more analysis modules 102 that may be configured to perform various tasks according to some embodiments, such as the tasks explained with reference to FIGS. 1A and 1B. To perform these various tasks, the analysis module 102 may operate independently or in coordination with one or more processors 104, which may be connected to one or more storage media 106. A display device 105 such as a graphic user interface of any known type may be in signal communication with the processor 104 to enable user entry of commands and/or data and to display results of execution of a set of instructions according to the present disclosure.

The processor(s) 104 may also be connected to a network interface 108 to allow the individual computer system 101A to communicate over a data network 110 with one or more additional individual computer systems and/or computing systems, such as 101B, 101C, and/or 101D (note that computer systems 101B, 101C and/or 101D may or may not share the same architecture as computer system 101A, and may be located in different physical locations, for example, computer systems 101A and 101B may be at a well drilling location, while in communication with one or more computer systems such as 101C and/or 101D that may be located in one or more data centers on shore, aboard ships, and/or located in varying countries on different continents).

A processor may include, without limitation, a microprocessor, microcontroller, processor module or subsystem, programmable integrated circuit, programmable gate array, or another control or computing device.

The storage media 106 may be implemented as one or more computer-readable or machine-readable storage media. Note that while in the example embodiment of FIG. the storage media 106 are shown as being disposed within the individual computer system 101A, in some embodiments, the storage media 106 may be distributed within and/or across multiple internal and/or external enclosures of the individual computing system 101A and/or additional computing systems, e.g., 101B, 101C, 101D. Storage media 106 may include, without limitation, one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that computer instructions to cause any individual computer system or a computing system to perform the tasks described above may be provided on one computer-readable or machine-readable storage medium, or may be provided on multiple computer-readable or machine-readable storage media distributed in a multiple component computing system having one or more nodes. Such computer-readable or machine-readable storage medium or media may be considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 100 is only one example of a computing system, and that any other embodiment of a computing system may have more or fewer components than shown, may combine additional components not shown in the example embodiment of FIG. 2, and/or the computing system 100 may have a different configuration or arrangement of the components shown in FIG. 2. The various components shown in FIG. may be implemented in hardware, software, or a combination of both hardware and software, including one or more signal processing and/or application specific integrated circuits.

Further, the acts of the processing methods described above may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of the present disclosure.

The methods disclosed herein suggest methods for the use of an existing morphological tool to describe the mineral framework of an aggregate, a direct application of which being the ability to predict the onset of grain crushing in a rock subjected to an increasing effective compressive stress such as in the case of subsurface fluid reservoir depletion

REFERENCES CITED IN THE PRESENT DISCLOSURE INCLUDE THE FOLLOWING

1. Hilpert, M. and C. T. Miller. 2001. Pore-morphology based simulation of drainage in totally wetting porous media. *Advances in Water Resources* 24: 243-255.
2. Silin, D. B. and T. W. Patzek. 2006. Pore space morphology analysis using maximal inscribed spheres. *Physica A: Statistical and Theoretical Physics* 371(2): 336-360.
3. Pittman, E. D. 1992. Relationship of porosity and permeability to various parameters derived from mercury injection—capillary pressure curves for sandstone. *American Association of Petroleum Geologists Bull.* 76(2): 191-198.
4. Zhang, J., T.-f. Wong, and D. M. Davis. 1990. Micromechanics of pressure-induced grain crushing in porous rocks. *J. Geophys. Res.* 95: 341-352.
5. Wong, T.-f, C. David, and W. Zhu. 1997. The transition from brittle faulting to cataclastic flow in porous sandstones: Mechanical deformation. *J. Geophys. Res.* 102: 3009-3025.
6. Fredrich, J. T., D. L. Lakshtanov, N. M. Lane, E. B. Liu, C. S. Natarajan, D. M. Ni, and J. J. Toms. 2014. Digital Rocks: Developing an emerging technology through to a proven capability deployed in the business. In *Proceedings of the Society of Petroleum Engineers Annual Technical Conference and Exhibition*, Amsterdam, The Netherlands, 27-29 Oct. 2014.
7. Rasband, W. S. 1997-2015. ImageJ, U. S. National Institutes of Health, Bethesda, Md., USA, http://imagej.nih.gov/ij/.
8. Dougherty, R. and K. Kunzelmann. 2007. Computing local thickness of 3D structures with ImageJ. *Microsc. Microanal.* 13: 1678-1679.
9. Zhu, W., L. Montesi, and T.-f Wong. 2007. A probabilistic damage model of stress-induced permeability anisotropy during cataclastic flow. *J. Geophys. Res.* 112: B10207
10. Brzesowsky, R. H., C. J. Spiers, C. J. Peach, and S. J. T. Hangx. 2014. Time-independent compaction behavior of quartz sands. *J. Geophys. Res. Solid Earth* 119: 936-956.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A method for analyzing a rock sample, comprising:
    entering into a computer a digital representation of a three dimensional image of the rock sample;
    in the computer, separating a three dimensional image of the rock sample into rock grain and pore space portions;
    in the computer, performing maximal inscribed sphere analysis on each voxel in the image to determine a local thickness;
    in the computer, determining proxies for at least one of grain size distribution, mean grain size and grain size standard deviation from the values of local thickness, the determining proxies comprising at least one of;
    (a) determining the proxies directly by assimilating the local thickness distribution to a grain size distribution,
    (b) treating a solid fraction as an aggregate of spherical particles, then obtaining a particle count by dividing a population of each bin in the distribution by the volume of a sphere corresponding to a diameter or thickness associated with that bin, or
    (c) treating the solid fraction as two-dimensional disks, then obtaining a particle count by dividing a population of each bin in the distribution by a cross sectional area corresponding to the diameter or thickness associated with that bin;
    in the computer, determining a highest local thickness and retaining a number of voxels having the highest local thickness;
    in the computer, determining whether the highest local thickness voxels individually participate in a cluster that is connected to either (i) one of all six faces or (ii) one of two parallel faces of the probed volume;
    in the computer, decreasing the local thickness by a predetermined increment and determining whether voxels with the new local thickness participate in a cluster that includes the previously selected voxels and that is connected to either one of all six faces or one of two parallel faces of an analyzed volume;
    in the computer, determining if a lowest value is reached and repeating the decreasing and determining whether the voxels with the new local thickness participate in a cluster that includes the previously selected voxels and that is connected to either one of all six faces or one of two parallel faces of the analyzed volume and determining if a lowest value is reached until a lowest value is reached;
    in the computer, generating a table from sequentially retained voxels that corresponds to a distribution of volumes that constitutes volume increments invaded when simulating acquisition of a 'mercury injection capillary pressure' (MICP) test;
    in the computer, determining the local thickness that corresponds to the maximum volume increment in the distribution;
    in the computer, defining a characteristic contact diameter as being that value of local thickness;
    in the computer, defining a characteristic contact radius as being half the value of the characteristic contact diameter;
    in the computer, determining the anisotropy of the characteristic contact diameter by running sequentially directional analysis along three principal directions of the probed volume;
    in the computer, using the local thickness cluster at the time of maximum volume increment as an alternate base for the determination of grain size distribution, mean grain size and grain size standard deviation;
    in the computer, defining the stress intensification coefficient as the ratio of a characteristic contact dimension to a mean grain dimension; and
    in the computer, using one or all of the proxies, dimensions and coefficients obtained during the analysis to determine at least one mechanical property of the rock sample, wherein the at least one mechanical property comprises at least one of an elastic property, a mechanical strength and compaction behavior.

2. The method of claim 1 wherein the at least one mechanical property comprises static bulk modulus.

3. The method of claim 1 wherein the at least one mechanical property comprises Young's modulus.

4. The method of claim 1 wherein the at least one mechanical property comprises shear modulus.

5. The method of claim 1 wherein the at least one mechanical property comprises at least one of compressional and shear wave velocity.

6. The method of claim 1 wherein the at least one mechanical property comprises compaction associated with pore collapse.

7. The method of claim 1 wherein the mechanical strength is determined isotropically.

8. The method of claim 1 wherein the mechanical strength is determined multiaxially so as to determine the presence of anisotropy.

9. A method for analyzing a rock sample, comprising:
   entering into a computer a digital representation of a three dimensional image of the rock sample;
   in the computer, separating a three dimensional image of the rock sample into rock grain and pore space portions;
   in the computer, performing maximal inscribed sphere analysis on each voxel of the rock grain portion in the image to determine a local thickness;
   in the computer, determining proxies for at least one of grain size distribution, mean grain size and grain size standard deviation from the values of local thickness; and
   in the computer, using at least one of the proxies to determine at least one mechanical property of the rock sample, wherein the at least one mechanical property comprises at least one of an elastic property, a hydrostatic mechanical strength, a mechanical strength and compaction behavior.

10. The method of claim 9 wherein the determining proxies comprises at least one of:
   (a) determining the proxies directly by assimilating the local thickness distribution to a grain size distribution;
   (b) treating a solid fraction as an aggregate of spherical particles, then obtaining a particle count by dividing a population of each bin in the distribution by the volume of a sphere corresponding to a diameter or thickness associated with that bin; and
   (c) treating the solid fraction as two-dimensional disks, then obtaining a particle count by dividing a population of each bin in the distribution by a cross sectional area corresponding to the diameter or thickness associated with that bin.

11. The method of claim 9 wherein the at least one mechanical property comprises static bulk modulus.

12. The method of claim 9 wherein the at least one mechanical property comprises Young's modulus.

13. The method of claim 9 wherein the at least one mechanical property comprises shear modulus.

14. The method of claim 9 wherein the at least one mechanical property comprises at least one of compressional and shear wave velocity.

15. The method of claim 9 wherein the mechanical strength is determined multiaxially so as to determine the presence of anisotropy.

16. The method of claim 9 wherein the mechanical strength is determined isotropically.

* * * * *